United States Patent [19]
Casey et al.

[11] Patent Number: 5,686,275
[45] Date of Patent: Nov. 11, 1997

[54] SYNTHESIS OF HOMOCHIRAL 2-HYDROXY ACIDS

[75] Inventors: Guy Casey, Exeter; Thomas Lee, deceased, late of Bristol, both of Great Britain; Victor Lee, administrator; Eileen Ann Lee, administratrix, both of Telford, United Kingdom

[73] Assignee: Genzyme Ltd., Suffolk, Great Britain

[21] Appl. No.: 256,120

[22] PCT Filed: Dec. 23, 1992

[86] PCT No.: PCT/GB92/02396

§ 371 Date: Aug. 26, 1994

§ 102(e) Date: Aug. 26, 1994

[87] PCT Pub. No.: WO93/13215

PCT Pub. Date: Jul. 8, 1993

[30] Foreign Application Priority Data

Dec. 23, 1991 [GB] United Kingdom ............... 92 27249.2
Aug. 10, 1992 [GB] United Kingdom ............... 92 16929.1

[51] Int. Cl.$^6$ ............................ C12P 7/42; C07D 307/33
[52] U.S. Cl. ........................ 435/146; 435/190; 435/280
[58] Field of Search ............................... 435/146, 280

[56] References Cited

U.S. PATENT DOCUMENTS 5,098,841  3/1992  Ghisalba .

FOREIGN PATENT DOCUMENTS 2003767  5/1990  Canada .
0380689  8/1990  European Pat. Off. .
0394448  10/1990  European Pat. Off. .

OTHER PUBLICATIONS

Casey, G. et al. (1992) "Enantioselective Reduction of B, X–Unsaturated a–Keto Acids Using Bacillus Stearothermophilus Lactate Dehydrogenase: A New Route To Functionalised Allyic" *Tetrahedron Letters*, 33(6):817–820.
Kim, M. et al. (1991) "Synthesis of Optically Pure (R)–2–Hydroxy Acids Using D–Lactate Dehydrogenase" *J Chem. Soc., Chem. Commun.*, 326–327.
Ziegler, T. et al. (1990) "A Convenient Route to (R)–a–Hydroxy Carboxylic Acids and (2R)–1–Amino–2–alkanols from (R)–Cyanohydrons" *Synthesis*, Jul.:575–578.
Kalaritis, P. et al. (1990) "Kinetic Resolution of 2–Substituted Esters Catalyzed by a LIbase Ex. Pseudomonas fluorescens" *J. Organ. Chem.*, 55:812–815.
Corey, E. et al. (1990) "A New System For Catalytic Enantioselective Reduction of Achiral Ketones to Chiral Alcohls. Synthesis of Chiral a–Hydroxy Acids" *Tetrahedron Letters*, 31(5):611–614.

Chan, P. et al. (1990) "Preparation of Enantiomerically Enriched a–Hydroxy Acid Derivatives From a–Alkoxyorganostannanes" *Tetrahedron Letters*, 31(14):1985–1988.
Bur, D. et al. (1989( "An evaluation of the substrate specificity and asymmetric synthesis potential of the cloned L–lactate dehydrogenase from Bacillus stearothermophilus" *Can. J. Chem.*, 67:1065–1070.
Simon E. et al. (1989) "D–Lactate Dehydrogenase–Substrate Specificity and Us eas a Catalyst in the Synthesis of Homochiral 2–Hydroxy Acids" *Applied Biochemistry and Biotechnology*, 22:169–179.
Francotte, E. et al. (1987) "Analytic and Preparative Resolution of Racemic y–and o– Lactones by Chromatography on Cellulose Triacetate, RElationship between Elution Order and Absolute Configuration" *Helvetica Chimica Acta*, 70:1569–1582.
Brown, H.C. et al. (1986) "Asymmetric Reduction of a–Keto Esters with Potassium" *J. Org. Chem.*, 51:3396–3398.
Evans, D. et al. (1985) "Asymmetric Oxygenation of Chiral Imide Enolates. A General Approach to the Synthesis of Enantiomerically Pure a–Hydroxy Carboxylic Acid Synthons" *J. Am. Chem. Soc.*, 197:4346–4348.
Hirschbein, B. et al. (1982) "Laboratory–Scale Enzymatic/ Chemical Syntheses of D– and L–B–Chlorolactic Acid and D–L–Potassium Glycidate" *J. AM. Chem. Soc.*, 104:4458–4460.
Dale, J. et al. (1969) "a–Methoxy–a–trifluoromethylphenylacetic Acid, a Versatile Reagent for the determination of Enantiomeric Composition of Alcohols and Amines" *The Journal of Organic Chemistry*, 34(9):2543–2549.
Meister, A. et al. (1948) "Enzymatic Hydrolysis of 2,4–Diketo Acids" *J. Biol. Chem.*, 175:573–588.

*Primary Examiner*—Herbert J. Lilling
*Attorney, Agent, or Firm*—William G. Gosz

[57] ABSTRACT

A process for the production of a homochiral 2-hydroxy carboxylic acid or salt thereof corresponding to general formula (I), wherein R represents one of formulae (II), (III), (IV), (V), wherein R' represents straight- or branched-chain alkyl or phenyl optionally para-substituted with methyl, methoxy, nitro or amino; and R" represents hydrogen, halogen or phenyl optionally para-substituted with methyl, methoxy, nitro or amino; and M represents hydrogen or a salt-forming moiety; characterized in that it comprises reducing a corresponding 2-keto carboxylic acid or salt thereof using a (R)- or (S)-2-oxo carboxylic acid dehydrogenase, inter alia, is disclosed.

6 Claims, No Drawings

SYNTHESIS OF HOMOCHIRAL 2-HYDROXY ACIDS

This invention relates to chiral synthesis; more particularly, it relates to the synthesis of certain homochiral 2-hydroxy acids using 2-oxo carboxylic acid dehydrogenases as versatile catalysts capable in many cases of preparation of both (R) and (S) isomers at the alpha hydroxy group.

The synthesis of chiral 2-hydroxy acids is of considerable importance, since these compounds are versatile synthetic intermediaries which may be converted to a variety of compounds with retention of chirality at C-2, including epoxides, alkyl esters, hydrazinyl esters, α-N-alkoxyamino esters and α-amino esters. In general, reactions involving nucleophilic substitution at the 2-position are optimally effected via the corresponding 2-triflate esters which are generated in situ and reacted directly with the chosen nucleophile.

The availability of chiral 2-hydroxy acids and esters possessing an additional prochiral functional group in the side chain, offers enormous potential for the synthesis of compounds containing two or more chiral centres. For this purpose, the hydroxyl group or C-2 is expected to provide an internal control element, facilitating stereoselective transformations of the prochiral functional group. In the case of β,γ-unsaturated compounds, expoxidation would give access to Sharpless-type intermediates, and dehydroxylation would produce polyols which may have utility in carbohydrate synthesis. In the case of the 4-oxo compounds, diastereoselective ketone reduction would provide either syn- or anti-1,3-diols, dependant on choice of conditions.

Chemistry offers, both in its more traditional forms and increasingly via enzyme-catalysed reactions, methods with potential for the synthesis of the compounds of particular interest.

2-hydroxy acids and esters are valuable synthetic entities and much effort has been expended in the development of methods for the preparation thereof in chiral form and examples of chemical and enzymatic methods are described below. The main limitations of the chemical procedures are technical, since the key transformations all involve the use of water-sensitive reagents at low temperature. With the exception of enone reduction, product chirality arises in a stoichiometric sense, either from chiral auxiliary (substrate control), or from a bulky chiral reductant (reagent control).

Asymmetric reduction of 2-keto esters using the chiral borane potassium 9-Q-DIPGF-9-BBNH (Brown H. C., et al, J. Org. Chem., (1986), 51, 3396) requires a stoichiometric quantity of the complex reducing agent and currently only provides access to 2-hydroxy esters of (S)-absolute configuration.

Hydroxylation of chiral oxazolidone enolates with oxaziridine oxidants (Evans, D. A., et al, J. Am. Chem Soc., (1985) 102, 4346) requires that, in order to obtain homochiral 2-hydroxy esters, this chromatographic resolution of the 2-hydroxy imide be undertaken prior to methanolysis. This process gives poor yields in the case of hindered derivatives (e.g. R represents Pr, Bu'). The use of valine-derived auxiliary provides a complementary route to (S)-2-hydroxy esters.

Carboxylation of chiral α-alkoxycarbanions (Chan C. M. & Chong J. M., Tet. Lett., (1990), 31, 1985) requires a stoichiometric quantity of the costly reducing agent (S)-BINAL-H and disposal of hazardous tin residues after the transmetallation stage. The use of (R)-BINAL-H in the first stage provides a complementary route to (R)-2-hydroxy acids.

Enantioselective reduction of enones catalysed by chiral oxazaborolidines, (Coney, G. J. & Bakshi R. K., Tet. Lett., (1990), 31, 611) derives chirality from a catalytic source in contrast to the above methods. The availability of the optical antipode of the catalyst provides a complementary route to the opposite enantiomeric series. A sequence of four chemical conversions are required in order to transform initially formed chiral alcohol to the 2-hydroxy ester with obvious cost and yield implications.

The published use of enzymes found in formation of chiral α-hydroxy acids includes (R)oxynitrilase and lipase based routes.

(R)-oxynitrilase catalysed synthesis of chiral cyanohydrins by hydrolysis (Zeigler, T., et al., Synthesis, (1990), 575) gives access to (R)-2-hydroxy acids only. A highly toxic water-free preparation of hydrogen cyanide is required for the enzymatic reaction, which gives variable enantioselection to as low as 74%.

Resolution of racemic 2-hydroxy esters catalysed by *Pseudomonas flourescens* lipase (Kalaritis P., et al., J. Org. Chem., (1990), 55, 812) is one of many examples of enzymatic kinetic isomer resolution. This method is inherently flawed since yields of a particular enantiomer are limited to a maximum of 50% from the resolutions of the unsymmetrical substrate. In practice, the percentage conversion has to be carefully controlled in order to achieve high optical purities which further reduce the yield.

Since 1950, a number of workers have investigated the reduction of 2-oxo carboxylic acids catalysed by S-LDH. For these studies, enzymes isolated from a variety of natural sources have been employed, including those obtained from mammalian tissues (e.g. rabbit muscle and beef heart) and bacteria (e.g. *Bacillus stearothermophilus*). Although these enzymes exhibit small variations of amino acid sequences in the periphery of the protein framework, those residues in and around the active site, responsible for catalysis of the 2-oxo acid/2-hydroxy acid inter-conversion, are conserved. For a given 2-oxo acid, a given enzyme activity may be examined by UV spectroscopy and quantified in terms of the Michaelis constant, Km, and the catalytic turnover, Kcat.

The basis for this assay procedure is the strong absorbance at 340 nm of the reduced cofactor NADH compared to the oxidised cofactor $NAD^+$ and the diminution of absorbance with concentration of NADH. The diminution of absorbance, which is directly proportional to the concentration of NADH, may be used to estimate the rate of enzymatic reduction. This technique is limited by several factors including the purity of the enzyme, where the presence of other enzyme activities may lead to oxidation of the NADH and the assumption that the oxidation of NADH activity correlates to the formation of the expected product.

Approximately fifty 2-oxo acids have been described in the literature as exhibiting measurable activity against S-LDH as determined by following the course of NADH oxidation.

The key requirement of a chemical biocatalytic reduction is very high isomeric purity and high chemical yield which are unknown for most of the reactions described in the literature and thus the utility thereof in a chemical reaction remains to be demonstrated. For use in an industrial biocatalytic reduction, further criteria must be satisfied, such as cost effectiveness over other methods, which is generally observed as a combination of substrate turnover by the enzyme and its durability.

Of the fifty compounds identified, only in some cases have preparative-scale experiments been performed, in order to characterise the product 2-hydroxy acid and to establish the enantioselectivity of the reduction. For these reactions, a catalytic amount of NADH is employed in conjunction with a regenerating system, requiring a second enzyme, usually formate dehydrogenase (FDH), which utilises NAD⁺ in the oxidation of formate ion to carbon dioxide as described by Shaked Z. & Whitesides G. M. (J. Am. Chem. Soc., (1980), 102, 7105).

This method provides (S)-2-hydroxy acids in good chemical yields and high optical purities, as indicated for the six substrates in Table 1 below. Entry 10 serves to illustrate the reduction of a substrate showing reactivity only 0.3% of that for pyruvate. This particular reaction is limited by the requirement for the allosteric activator fructose 1,6-bisphosphate (FBP) and takes 10.5 days to proceed to completion. This compares to a typical reaction time of 1–3 days in other cases.

In order to obtain 2-hydroxy acids with (R)-absolute configuration, reduction of 2-oxo acids catalysed by R-LDH has also been investigated. Recent studies (Simon, et al., Appl. Biochem. Biotechnol., (1989), 22, 169 and Kim M. J. & Kim J. Z. J., Chem. Soc. Chem. Commun., (1991), 326) have focussed on R-LDH from *Leuconostoc mesenteroides* (LM-R-LDH) and *Staphylococcus epidermidis* (SE-R-LDH). Only nine compounds have been shown to exhibit measurable activity and of these only the four compounds shown in Table 2 below have been reduced on a preparative scale.

The use of 2-oxo carboxylic acid dehydrogenases as catalysts for chiral reductions has to date been restricted to only a limited range of 2-oxo carboxylic acid substrates. Further compounds have been subject to certain spectrophotometric experiments and infer that they are reduced by enzymatic activity. The success of these reactions is left to interpretation not to analysis. The compounds investigated as substrates have tended to anticipate the boundaries of possibility of useful reduction with 2-oxo carboxylic acid dehydrogenases.

The direct formation of the homochiral 2-hydroxy acid could be performed using 2-oxocarboxylic acid dehydrogenases if substrate specifity was sufficiently broad to overcome the perceived limitation of turnover rate required for a process of anything more than academic curiosity.

The results of enzyme activity determinations with the present substrates were not particularly encouraging towards the use of the enzymes on a preparative scale as the very low turnover 0.6%–3% of the natural substrate of pyruvate which, when obtained, was expected to compromise the success of the chemical conversion in terms of time, yield, enantiomeric purity and cost effectiveness.

The examination of these lactate dehydrogenase enzymes for suitability was simply as one of the myriad of possibilities with no particular expectation of a result with any commercial utility, but simply to aid the design by site-directed mutagenesis of further, more useful catalysts. These enzymes were thus examined with no real incentive, but, notwithstanding, it was found that a useful process could be obtained from this most unpromising start.

The present invention provides a process for the production of a homochiral 2-hydroxy carboxylic acid or salt thereof corresponding to the following general formula:

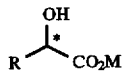

wherein

R represents one of the following:

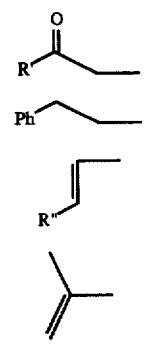

wherein R' represents straight- or branched-chain alkyl or phenyl optionally para-substituted with methyl, methoxy, nitro or amino; and R" represents hydrogen, halogen or phenyl optionally para-substituted with methyl, methoxy, nitro or amino;

and

M represents hydrogen or a salt-forming moiety; characterized in that it comprises reducing a corresponding 2-keto carboxylic acid or salt thereof using a (R)- or (S)-2-oxo carboxylic acid dehydrogenase.

Examples of 2-hydroxy carboxylic acids or salts thereof preferably produced by the present process are given in Table 3 below. Generally, a (R)- or (S)- lactate dehydrogenase, which may be obtained from *Bacillus stearothermophilus* or *Staphlococcus epidermidis*, is used for the present purposes. Such a reduction is often effected in combination with a recycling NADH reaction. With reference to the above-defined general formula, the salt-forming moiety, M, may represent sodium or potassium and/or the alkyl group, R', may have up to 6 carbon atoms in preferred cases.

The present invention further provides a process for the production of a syn- or anti-syn lactone having two chiral centres characterized in that it comprises the chemical reduction of a 4-keto derivative of a homochiral 2-hydroxy carboxylic acid or salt thereof produced by a process as described above or an ester thereof.

The present invention also provides a syn- or anti-syn lactone characterized in that it corresponds to the following general formula:

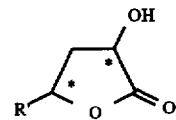

wherein R' is as defined above.

As will be appreciated from the foregoing, there have now been identified 2-oxo carboxylic acid substrates for enantioselective reduction using lactate dehydrogenases obtained from *Bacillus stearothermophilus* (BS-S-LDH; Genzyme Biochemicals) and *Staphylococcus epidermidis* (SE-R-LDH; Sigma Chemical). Reductions have been carried out on a preparative scale to permit the isolation and characterisation of 2-hydroxy acids and possessing either (S)- or (R)-absolute configuration at the 2- position.

The following compounds have now been prepared by reduction using the enzyme lactate dehydrogenase obtained from *Bacillus stearothermophilus* and additionally for some compounds using the enzyme lactate dehydrogenase obtained from *Staphylococcus epidermidis* which produces the alternative (R) stereochemistry.

Compounds prepared by LDH reduction.

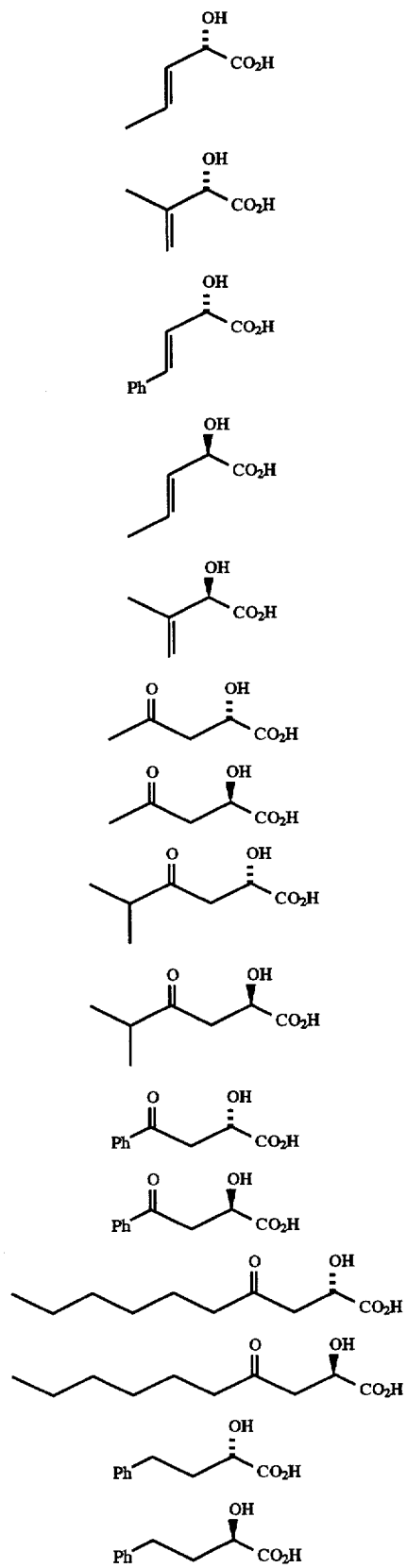

BS-S-LDH catalysed reduction of 2-keto acids, precursors to compounds 1, 2, 3, 6, 8, 10 and 14, has been carried out on a preparative scale (1–15 mMol) using the standard formate/formate dehydrogenase combination to cycle the cofactor NADH in situ. Compounds 4, 5, 7, 9, 11, 13 and 15 were also prepared by reduction using SE-R-LDH. In each reaction the optimum pH was maintained by periodic addition of dilute hydrochloric acid.

The stereoselectivity of each reduction was determined by NMR and capilliary GC analyses of the (+)-MPTA Mosher derivative, (Dale, J. A., et al. J. Org. Chem., (1969), 34, 2543) in comparison with a racemic standard. This is the standard literature protocol for chiral analysis of 2-hydroxy acid derivatives and is sensitive enough to detect $\leq 0.5\%$ of the minor diastereoisomer.

The Mosher derivatives were prepared by esterification of the 2-hydroxy acid, followed by acylation with (+)-MTPA-Cl.

For all enzymatic reductions, the substrates were in the form of sodium or potassium salts due to improved solubility and stability over the free acid.

The preparation of a structurally diverse range of (S) and (R) 2-hydroxy-4-oxo acid derivatives as shown by compounds 6 to 13 above presents opportunities for introduction of further chirality by reduction of the prochiral ketone function. The hydride reduction of the 4-carbonyl groups allows the stereoselective synthesis of substituted 2-hydroxy butyrolactones.

The result of these experiments illustrates that a broad range of diketo acid salts may be readily converted to any one of four diasteriomeric lactones depending on the choice of conditions employed for enzymatic (S or R-LDH) and chemical (syn- or anti-selective) reduction.

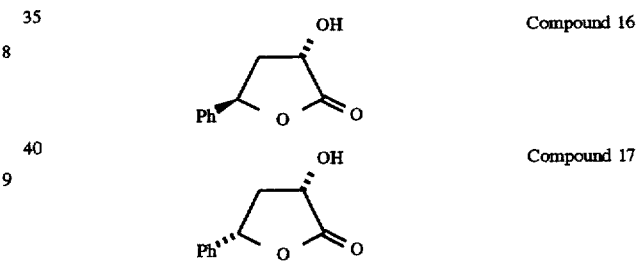

2,4-dioxopentanoate, the starting material for compounds 6 and 7, was prepared as the disodium salt by the Claisen condensation of acetone and diethyl oxalate, followed by treatment with two equivalents of aqueous sodium hydroxide, with yields of 77% and 89%, respectively.

The disodium salts of the dioxoacid starting materials for compounds 8, 9, 10, 11, 12 and 13 were prepared using a two step procedure based on the work of Meister A. (J. Biol. Chem., (1948), 175, 573), using diethyl oxalate and the appropriate methyl ketone. Recoveries were comparable to those obtained with the similar procedure used for the synthesis of 2,4-dioxopentanoate described above.

2-oxo-4-phenyl-butanoate, the starting material for compounds 14 and 15, (E)-2-oxo-3-pentenoate, starting material for compounds 1 and 4 and 3-methyl-2-oxo-3-butenoate, the starting material for compounds 2 and 5, were all prepared as the sodium salts. The method employed the low temperature addition of 1 equivalent of the appropriate Grignard reagent to diethyl oxalate, followed by controlled hydrolysis with 1 equivalent of sodium hydroxide. The yields from the two stage reactions are shown below.

| Product | Yield of Ester From Originals | Yield of Sodium Salt from Ester |
|---|---|---|
| 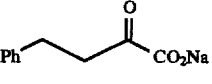 Ph–CH2–C(=O)–CO2Na | 86% | 79% |
| 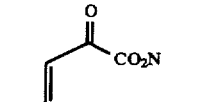 CH3–CH=CH–C(=O)–CO2N | 53% | 52% |
| 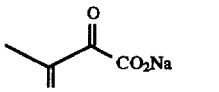 (CH3)2CH–C(=O)–CO2Na | 86% | 42% |

(E)-2-oxo-4-phenyl-3-butenoate, the starting material for compound 3, was prepared as the potassium salt by the aldol condensation of benzaldehyde and pyruvic acid, achieving a yield of 72%. This synthesis procedure was applied to the alcohol condensation of pyruvic acid and para-substituted benzaldehydes allowing the preparation of the following potential substrates:

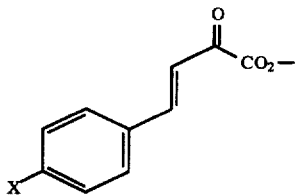

wherein X represents Me, MeO or $NO_2$.

Synthesis of (E)-(S)-2-hydroxy-4-phenyl-3-butenoic acid (Compound 3)

A solution of potassium (E)-2-oxo-4-phenyl-3-butenoate (214 mg, 1.0 mmol) and sodium formate (156 mg, 2.3 mmol) in Tris buffer (5 mM, pH adjusted to 6.0 with 2M HCl; 50 ml) was deoxygenated by bubbling through nitrogen for 30 minutes. NADH (14 mg, 0.02 mMol), dithiothreitol (5 µl of a 1M aqueous solution), formate dehydrogenase (10 mg, 5 U) and S-lactate dehydrogenase (*Bacillus stearothermophilus*, Genzyme; 5 mg lyophilised powder=0.7 mg protein, 300 U) were added successively to the solution at room temperature under nitrogen.

The mixture was stirred under nitrogen for 47 hours, with periodic addition of dilute HCl (0.2M, 3.4 ml) from a burette to maintain the pH in the range 6.0–6.2. After acidification to pH 2 and saturation with sodium chloride, the mixture was filtered under gravity. The filtrate was subject to a normal ethyl acetate (4×50 ml) work-up with brine (50 ml) wash to afford the title compound (3) as an amorphous white solid (151 mg, 85%). This material was pure by $^1$H-NMR; re-crystallisation from ether/ethyl acetate provided an analytically pure white solid, m.p. 135°–6° C., $[\alpha]_D^{27}$=+91.0° (c=1.875, MeOH) δ (270 MHz, $d_6$-acetone) 7.49–7.44 and 7.38–7.22 (5H, 2 m, Ph), 6.84 (1H, dd, J 1.6 and 15.9 Hz, C-4-H), 6.43 (1H, dd, J 5.5 and 15.9 Hz C-3-H) and 4.86 (1H, dd, J 1.6 and 5.5 Hz, C-2-H).

NMR analysis of the Mosher derivative indicated a mixture of diastereoisomers in a ratio of 100:1, corresponding to an enantiomeric excess(ee) of ≧98% for (S)-2-hydroxy-4-phenyl-3-butenoic acid.

Substitution of (E)-2-oxo-4-phenyl-3-butenoate by analogue molecules with para-substitutions demonstrated enzyme reduction with Me, MeO and $NO_2$.

With Me and MeO substitution, complete conversion was obtained after 36 hours and 48 hours, respectively, with isolated yields of 38% and 25%. Analysis of the reaction was performed by $^1$H-NMR demonstrating the viability of the substrates.

Synthesis of (S)-(E)-2-hydroxy-3-pentenoic acid (Compound 1)

(S)-lactate dehydrogenase from *Bacillus stearothermophilus* (Genzyme, lyophilised powder; 2000 U) and formate dehydrogenase (Boehringer; 5 U) were added to a deoxygenated solution of sodium (E)-2-oxo-3-pentenoate (136 mg, 1.0 mmol) in Tris-HCl buffer (5 mM pH6; 20 ml) containing sodium formate (82 mg, 1.2 mM), NADH (7 mg, 0.01 mM) and dithiothreitol (0.002 mM).

The mixture was stirred at room temperature for 48 hours, with periodic addition of 0.2M HCl (3.4 ml) to maintain a pH of 6.0–6.2. Acidification to pH2, followed by saturation with salt, filtration, and ethyl acetate (3×20 ml) work-up with brine (20 ml) wash gave the product 2-hydroxy acid as a spectroscopically pure colourless oil (114 mg, 98%). δ (270 MHz, $d_6$-acetone) 6.03–5.89 (1H, m, C-4-H), 5.58 (1H, ddq, J 1.5, 6.2 and 15.2 Hz, C-3-H), 4.71–4.67 (1H, m inc. $^3J$ 6.2 Hz, C-2), 1.78–1.74 (3H, m inc. $^3J$ 6.6 Hz, C-4-$H_3$).

$^1$H-NMR analysis of the Mosher derivative of the corresponding methyl ester indicated a mixture of diastereoisomers in a ratio of 98.5:1.5, corresponding to an enantiomeric excess of ≧97% for the title compound.

Synthesis of (R)-(E)-2-hydroxy-3-pentenoic acid (Compound 4)

Using the general method above for Compound 1, with the substitution of S-LDH by R-LDH from *Staphylococcus epidermidis* (1000 units, 62 mg), the pH of the reaction was maintained at 7.5. The title compound was produced in the reaction at 100% and gave an identical NMR sepctrum to compound 1. The isolated yield was 92%. $^1$H-NMR analysis of the corresponding Mosher derivative indicated an enantiomeric excess of ≧98% for the title compound. The result was confirmed using capillary GC measurements.

Synthesis of (S)-2-hydroxy-3-methyl-3-butenoic acid (Compound 2)

(S)-lactate dehydrogenase from *Bacillus stearothermophilus* (Genzyme, lyophilised powder; 1200 U) and formate dehydrogenase (Boehringer; 5 U) were added to a deoxygenated solution of sodium 3-methyl-2-oxo-butenoate (136 mg, 1 mmol) in Tris-HCl buffer (5 mM; pH6; 67 ml) containing sodium formate (190 mg, 2.8 mmol), NADH (14 mg, 0.02 mmol) and dithiothreitol (0.007 mmol). The mixture was stirred at room temperature under nitrogen for 76 hours, with periodic addition of 0.2M HCl (3.0 ml) to maintain a pH of 6.0–6.2. Acidification to pH2, followed by saturation with salt, filtration, and ethyl acetate (5×20 ml) work-up with a brine (20 ml) wash gave the product 2-hydroxy acid as a spectroscopically pure white solid, (76 mg, 66%). δ 5.21–5.20 (1H, m, 1H of C=$CH_2$), 5.11–5.10 (1H, m, 1H of C=$CH_2$), 4.69 (1H, brs, C-2-H), 1.82–1.81 (1H, m, C-3-$CH_3$).

$^1$H-NMR analysis of the Mosher derivative of the corresponding methyl ester indicated a mixture of diastereoisomers in a ratio of 200:1, corresponding to an enatiomeric excess of ≧99% for the title compound.

Synthesis of (R)-2-hydroxy-3-methyl-3-butenoic acid (Compound 5)

Using the general method above for Compound 2, with the substitution of S-LDH by R-LDH from *Staphylococcus epidermidis* (1000 units, 62 mg), pH of the reaction was maintained at 7.5. The title compound was produced in the reaction at 65% yield and gave an identical NMR spectrum to compound 2. $^1$H-NMR analysis of the corresponding Mosher derivatives indicated an enantiomeric excess of ≧99% for the title compound. This result was confirmed using capillary GC measurement.

Synthesis of (S)-methyl 2-hydroxy-4-oxo pentanoate (Compound 6)

A solution of the disodium salt of 2,-4-dioxopentanoic acid (2.61 g, 5 mmol) and sodium formate (1.53 g, 22.5 mmol) in Tris buffer (5 mM pH adjusted to 6.0 with 2M HCl; 100 ml) was de-oxygenated by bubbling through nitrogen for 30 minutes. NADH (106 mg, 0.15 mmol), dithiothreitol (1 µl of a 1M aqueous solution), formate dehydrogenase (75 mg, 37.5 U) and S-lactate dehydrogenase (*Bacillus stearothermophilus*, Genzyme; 25 mg lyophilised powder≡3.5 mg protein, 1500 U) were added successively to the solution at room temperature under nitrogen. The mixture was stirred under nitrogen for 72 hours, with periodic addition of HCl (0.5M; 19 ml) from a burette to maintain the pH in the range 6.0–6.2. After acidification to pH2, water was removed by rotary evaporation at 40° C., followed by evaporation to 0.5 mm Hg (~0.65 mbar). The residue was treated directly with anhydrous methanol (75 ml), trimethyl orthoformate (75 ml) and p-toluene sulphonic acid (0.57 g, 3 mmol). After stirring for 3 hours, a solution of sodium bicarbonate (0.50 g, 6 mM) in water (2 ml) was added to quench the reaction. Stirring was continued for 15 minutes then the mixture was dried (MgSO$_4$) and filtered through a pad of Celite, washing through with ethyl acetate (75 ml).

After concentration of the filtrate in vacuo, the residue was triturated with ethyl acetate (60 ml) and the mixture filtered through a pad of silica gel (Merck 9385), washing through with ethyl acetate (3×20 ml). The filtrate was concentrated to leave an amber oil (1.67 g), $^1$H-NMR analysis of which indicated a mixture of the title compound and the corresponding dimethyl acetal in a ratio of ca. 1:5. The oil was treated directly with acetone (Aldrich HPLC grade; 80 ml) and pyridinium p-toluene sulphonate (50 mg, 0.2 mmol). After stirring for an hour, aqueous bicarbonate (0.5 ml) was added to quench the reaction.

After drying (MgSO$_4$), filtration and concentration of the filtrate in vacuo, column chromatography (petrol/ethyl acetate, 1:1) gave the title compound as a pale yellow oil (1.07 g, 49%). δ (270 MHz, CDCl$_3$) 4.41 (1H, dd, J 4.2 and 6.2 Hz, C-2-H), 3.68 (3H, s, CO$_2$CH$_3$), 2.94–2.77 (2H, m, C-3-H$_2$), 2.11 (3H, s, C-5-H$_3$).

$^1$H-NMR analysis of the corresponding Mosher derivative indicated that homochiral (≧99% ee) product had been obtained with an [α]$_D^{24}$ value of −11.6° (c=3.35, Me$_2$CO).

Synthesis of (R)-methyl 2 hydroxy-4-oxopentanoate (Compound 7)

A solution of the disodium salt of 2,4-dioxopentanoic acid (0.52 g, 3 mmol) and sodium formate (0.24 g, 3.5 mmol) in Tris buffer (5 mM; pH corrected to 7.5 with 2M HCl; 20 ml) was de-oxygenated by bubbling through nitrogen for 30 minutes. NADH (28 mg, 0.04 mmol), dithiothreitol (2 ml of a 1M aqueous solution), formate dehydrogenase (20 U) and R-lactate dehydrogenase (*Staphylococcus epidermidis*, Sigma, 500 U) were added successively at room temperature under nitrogen. The mixture was stirred under nitrogen for 69 hours, with periodic addition of dilute HCl (0.5M; 2.6 ml) from a burette to maintain the pH in the range 6.0–6.2. After acidification to pH2, water was removed by rotary evaporation at 40° C., followed by evacuation to 0.5 mm Hg (~0.65 mbar). The residue was subject to methanolysis using methanol (15 ml), trimethylorthoformate (15 ml) and TsOH (100 mg, 0.53 mmol) over 5.5 hours. The mixture was concentrated under a stream of nitrogen and transacetylated with PPTS (10 mg) and acetone (20 ml) over 1.5 hours. The title compound was obtained as pale yellow oil (0.23 g, 53%), having identical spectroscopic properties to the (S)-enantiomer (compound 6). $^1$H-NMR analysis of the corresponding Mosher derivative indicated that homochiral (>0.99% ee) product had been obtained with an [α]$_D^{24}$ of +11.3° (c=2.2, Me$_2$CO).

Synthesis of (S)-2-hydroxy-5-methyl-4-oxohexanoic acid (Compound 8)

A solution of disodium salt of dimethyl 2,4-dioxopentanoic acid (404 mg, 2 mmol) and sodium formate (320 mg, 4.6 mmol) in Tris-buffer (5 mM, pH adjusted to 6.0 with 2M HCl) was de-oxygenated by bubbling through nitrogen for 30 minutes. NAD (2 mole %), dithiothreitol (10 µl of a 1M aqueous solution), formate dehydrogenase (10 U) and S-lactate dehydrogenase (*Bacillus stearothermophilus*, Genzyme, 600 U) were added to the solution at room temperature under nitrogen. The mixture was stirred under nitrogen for 60 hours, with periodic addition of HCl (0.5M, 2.6 ml) from a burette to maintain the pH in the range 6.0–6.2. After complete reduction was observed, the reaction mixture was acidified to pH 2.0 and saturated with sodium chloride, the mixture was subject to normal ethyl acetate extraction and brine wash. The title compound was isolated as a white solid at 72% recovery (0.23 g) δ (270 MHz, d$_6$-acetone) 4.53 (1 H, dd, J 5.3 and 6.2 Hz, C-2-H), 2.98–2.85 (2H, m, C-3-H$_2$), 2.67 (1H, septet, J 7.0 Hz, C-5-H), 1.06 (6H, d, J 7.0 Hz, C-5-Me$_2$). The melting point of the title compound was 66°–68° C. with an [α]$_D^{24}$ value (c=2.24, Me$_2$CO) of −14.8° H$^1$-NMR analysis of the corresponding Mosher derivative indicated on enantiomeric excess of ≧99% for the title compound.

Synthesis of (R)-2-hydroxy-5-methyl-4-oxohexanoic acid (Compound 9)

Using the general method above for compound 8 with the substitution of S LDH by R LDH from *Staphylococcus epidermidis* (500 units, 25 mg), the pH of the reaction was maintained at 7.5 over the 60 hour reaction. The title compound was recovered following ethyl acetate extraction, as a white solid at 75% yield (0.24 g) having identical spectroscopic properties to the (S)-enantiomer (compound 8). The title compound gave a melting point of 67°–68° C. and an [α]$_D^{24}$ value of (c=2.08 Me$_2$CO) 14.2°. $^1$H-NMR analysis of the corresponding Mosher derivative indicated an enantiomeric excess of ≧99% for the title compound.

Synthesis of (S)-2-hydroxy-4-oxo-4-phenylbutanoic acid (Compound 10)

Using the general method for compound 8, with phenyl-2,4-dioxopentanoic acid (472 mg, 2 mmol) and S-lactate dehydrogenase (*Bacillus stearothermophilus*, Genzyme, 300 units, 5 mg) at pH6, complete reduction was observed after 44 hours. The title compound was recovered as a white solid at 69% yield (0.27 g). δ (270 MHz, d$_6$-acetone) 8.06–8.02 (2H, m, Ar), 7.68–7.62 (1H, m, Ar), 7.57–7.51 (2H, m, Ar), 4.73 (1H, m, C-2-H), 3.50 (2H, d, J 5.3 Hz, C-3-H$_2$). Analysis of the material obtained a melting point of 132°–134° C. and an [α]$_D^{24}$ value (c=2.08, Me$_2$CO) of −1.6° $^1$H-NMR analysis of the corresponding Mosher derivative indicated an enatiomeric excess of ≧99% for the title compound.

Synthesis of (R)-2-hydroxy-4-oxo-4-phenylbutanoic acid (Compound 11)

Using the general method for compound 8, with the substitution of S-LDH by R-LDH from *Staphylococcus epidermidis* (500 units, 25 mg), phenyl-2,4-dioxopentanoic acid (472 mg, 2.0 mmol), complete reduction was observed in 43 hours, while maintaining the pH at 7.5. The title compound was recovered, following ethyl acetate extraction, as a white solid at 52% yield (0.20 g) having identical spectroscopic properties to the (S)-enantiomer (compound 10). The title compound gave a melting point of 128°–131° C. and an $[\alpha]^{24}$ value (c=2.58, Me$_2$CO) of 1.5°. $^1$H-NMR analysis of the corresponding Mosher derivative indicated an enantiomeric excess of ≧96% ee for the title compound.

Synthesis of (S)-2-hydroxy-4-oxodecanoic acid (Compound 12)

Using the general method for compound 8 with 2,4-dioxodecanoic acid (0.97 g, 4.0 mmol) and S-lactate dehydrogenase (*Bacillus stearothermophilus*, Genzyme, 600 units) with formate dehydrogenase (10 units), complete reduction was obtained in 55 hours. The title compound was obtained as a white solid at 72% yield (0.58 g) δ (270 Mhz, d$_6$-acetone) 4.55 (1H, dd, J 4.6 and 6.9 Hz, C-2-H), 2.96–2.79 (2H, m, C-3-H$_2$), 2.53–2.48 (2H, m, C-5-H$_2$), 1.57–1.49 (2H, m, C-6-H$_2$), 1.34–1.17 (6H, m, C-7, 8, 9-H$_2$), 0.88 (3H, t, J 6.6 Hz, C-10-H$_3$). Analysis of the product revealed a melting point of 69°–70° C. and an $[\alpha]^{24}$ value of –9.3° (c=2.39, acetone). $^1$H-NMR analysis of the corresponding Mosher derivative indicated an enantiomeric excess of ≧99% for the title compound.

Synthesis of (R)-2-hydroxy-4-oxodecanoic acid (Compound 13)

Using the general method for compound 8 with the substitution of S-LDH by R-LDH from *Staphylococcus epidermidis* (250 units), 2,4-dioxodecanoic acid (0.244 g, 1.0 mmol), complete reduction was obtained in 48 hours, while maintaining a pH of 7.5. The title compound was recovered following ethyl acetate extraction, at 65% yield (0.13 g) having identical spectroscopic properties to the (S)-enantiomer (compound 12). Analysis of the product revealed a melting point of 69°–71° C. and an $[\alpha]^{24}$ value of 9.4° (c=2.05, acetone). $^1$-NMR analysis of the corresponding Mosher derivative indicated an enantiomeric excess of ≧99% ee for the title compound.

Synthesis of (S)-2-hydroxy-4-phenyl butanoic acid (Compound 14)

A solution of sodium 2-oxo-4-phenyl butanoate (2.0 g, 10 mmol) and sodium formate (0.82 g, 12 mmol) in Tris buffer (5 mM, pH adjusted to 6.0 with 2M HCl; 250 ml) was deoxygenated by bubbling through nitrogen for 30 minutes. NADH (0.35 g, 0.5 mmol), dithiothreitol (25 μl of a 1M aqueous solution), formate dehydrogenase from yeast (Boehringer, 50 mg, 33 U) and S-lactate dehydrogenase from *Bacillus stearothermophilus*, (Genzyme, 96 mg lyphilised powder=13 mg protein, 5600 U) were added successively to the solution at room temperature under nitrogen. The mixture was stirred gently under nitrogen at 35°–40° C. for 94 hours, with periodic addition of dilute HCl to maintain pH in the range of 6.0–6.2. After acidification to pH3 and saturation with sodium chloride, the mixture was subjected to normal ethyl acetate (3×200 ml) work-up with a brine wash (200 ml) to leave a white solid (1.7 g, 94% recovery with residual starting material<10%). Recrystallisation from tetrachloromethane gave (S)-2-hydroxy-4-phenyl butanoic acid as an amorphous white solid (1.40 g, 77%) . δ (270 MHz, CDCl$_3$), 7.32–7.17 (5H, m, Ph), 4.27 (1H, dd, J 3.9 and 8.0 Hz, C-2-H), 2.83–2.74 (2H, m, C-4-H$_2$) and 2.25–1.95 (2H, m, C-3-H$_2$). The title compound gave a melting point of 111.5°–114° C. and an $[\alpha]_D^{22}$ value (c=2.02, EtOH) of 8.3°.

$^1$H-NMR and CGC analysis of the Mosher derivative of the corresponding methyl ester indicated that homochiral (>99% ee) product had been obtained.

Synthesis of (R)-2-hydroxy-4-phenyl butanoic acid (Compound 15)

A solution of sodium 2-oxo-4-phenyl butanoate (601 mg, 3.0 mmol) and sodium formate (0.34 g, 5 mmol) in Tris buffer (5 mM; pH adjusted to 7.5 with 2M HCl). NADH (43 mg, 0.06 mM), dithiothreitol (7.5 μl of a 1M aqueous solution), formate dehydrogenase from yeast (Boehringer; 20 mg, 10 U) and R-lactate dehydrogenase from *Staphylococcus epidermidis* (Sigma; 31 mg, 500 U) were added successively to the solution at room temperature under nitrogen. The mixture was stirred under nitrogen for 77 hours, with periodic addition of dilute HCl (0.5 m; 3.9 ml) to maintain the pH in the range of 7.4–7.6. After acidification to pH2 and saturation with sodium chloride, the mixture was filtered under gravity. The filtrate was subjected to a normal ethyl acetate (4×70 ml) work-up with brine wash (70 ml ) to afford (R)-2-hydroxy-4-phenyl butanoic acid (7) as an amorphous white solid (513 mg, 95%) having identical spectroscopic properties to the (S)-enantiomer (compound 14). The title compound gave a melting point of 113°–115° C. and an $[\alpha]_D^{22}$ value (c=2.21, EtOH) of –8.4°. $^1$H-NMR and capillary GC analysis of the Mosher derivative of the corresponding methyl ether indicated that homochiral (>99% ee) product had been obtained.

Synthesis of diasterioisomeric phenyl lactones (Compounds 16 and 17)

The investigation of the synthetic utility of the 4-oxo compounds (as illustrated by those described here as compounds 6–11) was exemplified with the hydride reduction of compound 10, (S)-2-hydroxy-4-oxo-4-phenylbutanoic acid and the corresponding methyl ester.

The following scheme illustrates the three reduction routes used and the ratio of compounds 16 and 17 obtained along with the overall yield.

| | | 10 | 16 | 17 |
|---|---|---|---|---|
| | Reduction conditions | | Relative Proportions | Overall Yield |
| (a) | NaBH$_4$/NaOH/H$_2$O | | 2:3 | 79% |
| (b) | 3eq DIBAL-H/THF –78° C. methyl ester of compound 10 | | 50:1 | 65% |
| (c) | i) Me$_4$N$^+$(AcO)$_3$BH$^-$ AcOH/MeCN–20° C. ii) NaOH/H$_2$O | | 1:6 | 90% |

Reagent (a) using sodium borohydride in aqueous alkali, followed by acidification to pH2 and extraction, produced a mixture of both diastereoisometric lactone compounds 16 and 17. These compounds were separated by column chromatography and the following spectroscopic data determined.

Spectroscopic data: 16 Vmax (film) 3422 br and 1776 cm$^{-1}$; δ ((CD$_3$)$_2$CO) 7.42–7.34 (5H, m, Ph), 5.72–5.68 (1H, m, C-4-H), 5.25 (1H, d, J 4.8 Hz, O-H), 4.57–4.50 (1H, m, C-2-H), 2.67–2.46 (2H, m, C-3-3H$_2$); δ$_c$ 176.3 (C-1) , 140.2, 128.9, 128.4, 125.7 (Ph), 78.9, 67.4 (C-2 and C-4) and 39.2 (C-3); m/z 178 (M$^+$; 6%), 134 (89%), 105 (39%) and 92 (100%), 17 Vmax (Nujol) 3369 br and 1762 cm$^{-1}$; δ ((CD$_3$)$_2$CO) 7.45–7.35 (5 H, m, Ph), 5.43 (1H, dd, J 5.4 and 10.9 Hz, C-4-H), 5.12 (1H, d, J 5.5 Hz), 4.78 (1H, ddd, J 5.5, 8.1 and 11.2 Hz), 3.01 (1H, ddd, J 5.3, 8.1 and 12.3 Hz, C-3-H) and 2.18–2.05 (1H, m, C-3-H); δ$_c$ 176.45, (C-1), 139.5, 128.8, 128.7, 126.1 (Ph), 76.8, 68.7 (C-2 and C-4) and 40.15 (C-3): m/z 178 (M$^+$; 12%), 134 (68%) and 92 (100%).

The assignment of relative steriochemistry to these products was made on the basis of $^1$H-NMR measurements, in particular an N. O. E enhancement of 4% between the C-2 methine hydrogen and aromatic signals of compound 16 which was absent from the spectrum of compound 17.

Excellent syn selectivity was observed for the diastereoselective reduction of β-hydroxy ketone derivatives using reagent (b) and achieving directly in the reaction 98% yield of the required isomer.

The use of the methyl ester allowed reversal of this selectivity when combined with reagent (c) prior to sequential treatment with aqueous alkali and dilute acid to effect ester hydrolysis and lactonisation. Yield of compound 17 by this process was 86% pure compared to the opposite enantiomers compound 16 directly in the reaction.

TABLE 1

Preparative scale reductions of 2-oxo-acids using S-LDH

| Substrate | S-LDH Source | Chemical Yield % | Optical Purity % ee | Reference |
|---|---|---|---|---|
| Cl-CH2-CO-CO2H | RM | 52 | >97 | 1 |
| H3C-CO-CO2H | RM | 99 | >99 | 2 |
| H3C-CO-CO2H | BS | 88 | >99 | 3 |
| H3C-CH2-CO-CO2H | RM | 97 | >99 | 2 |
| H3C-CH2-CO-CO2H | BS | 89 | >99 | 3 |
| cyclopropyl-CO-CO2H | RM | 94 | >99 | 2 |
| cyclopropyl-CO-CO2H | BS | 89 | >99 | 3 |
| Ph-CH2-CO-CO2H | RM | 96 | >99 | 2 |
| Ph-CH2-CO-CO2H | BS | 99 | >99 | 3 |
| (CH3)2CH-CO-CO2H | BS | 86 | >99 | 3 |

<sup>a</sup>NADH regenerated using glucose-6-phosphate and glucose-6-phosphate dehydrogenase.
<sup>b</sup>FBP included in reaction mixture
RM = Rabbit Muscle
BS = *Bacillis stearothermophilus*
Ref 1 Hirschbein B C & Whitesides G M J. Am. Chem. Soc., (1982), 104, 4458
Ref 2 Kim M H & Whitesides G M J. Am. Chem. Soc., (1988), 110, 2959
Ref 3 Bur D, et al. Can, J. Chem., (1989), 67, 1065

TABLE 2

Preparative scale reductios of 2-oxo acids using R-LDH

| Substrate | R-LDH Source | Chemical Yield % | Optical Purity % ee | Reference |
|---|---|---|---|---|
| H3C-CO-CO2H | LM | 95% | >98 | 1 |
| H3C-CO-CO2H | SE | 86 | >99 | 2 |
| Ph-CO-CO2H | LM | 98 | >98 | 1 |
| Ph-CO-CO2H | SE | 80 | >99 | 2 |
| cyclopropyl-CO-CO2H | SE | 86 | >99 | 2 |
| H3C-CH2-CO-CO2H | SE | 92 | >99 | 2 |

LM = *Leuconostoc mesenteroides*
SE = *Staphylococcus epidermis*
Ref 1 Simon E S, Playnte R & Whitesides G M Appl. Biochem. Biotechnol., (1989), 22, 169
Ref 2 Kim M J & Kim J Y J. Chem. Soc. Chem. Commun. (1991), 326

TABLE 3

Preparative scale reductions of present LDH substrates

| Substrate | Enzyme | Chemical Yield % | Optical Purity % ee |
|---|---|---|---|
| ONa-C=CH-CO-CH2-CO2Na | BS-S-LDH | 49<sup>a</sup> | >99 |
| ONa-C=CH-CO-CH2-CO2Na | SE-R-LDH | 53<sup>a</sup> | >99 |
| Ph-CH2-CO-CH2-CO2Na | BS-S-LDH | 77 | >99 |
| Ph-CH2-CO-CH2-CO2Na | SE-R-LDH | 95 | >99 |
| CH2=CH-CO-CH2-CO2Na | BS-S-LDH | 98 | >97 |
| CH2=CH-CO-CH2-CO2Na | SE-R-LDH | 92 | >98 |

TABLE 3-continued

Preparative scale reductions of present LDH substrates

| Substrate | Enzyme | Chemical Yield % | Optical Purity % ee |
|---|---|---|---|
| CH₂=C(CH₃)-C(O)-CO₂Na | BS-S-LDH | 66 | >99 |
| CH₂=C(CH₃)-C(O)-CO₂Na | SE-R-LDH | 65 | >99 |
| Ph-CH=CH-C(O)-CO₂K | BS-S-LDH | 85 | >98 |
| (iPr)C(ONa)=CH-C(O)-CO₂Na | BS-S-LDH | 72 | >99 |
| (iPr)C(ONa)=CH-C(O)-CO₂Na | SE-R-LDH | 75 | >99 |
| (n-C₆H₁₃)C(ONa)=CH-C(O)-CO₂Na | BS-S-LDH | 72 | >99 |
| (n-C₆H₁₃)C(ONa)=CH-C(O)-CO₂Na | SE-R-LDH | 65 | >99 |
| Ph-C(ONa)=CH-C(O)-CO₂Na | BS-S-LDH | 69 | >99 |
| Ph-C(ONa)=CH-C(O)-CO₂Na | SE-R-LDH | 52 | >96 |

*)after derivation of acid to methyl ester.

TABLE 4

¹H—NMR chemical shifts (δ) of (R)-Mosher derivatives prepared from compounds 1–15

R-CH(OH)-CO₂H (1,2,3,6,8,10,12,14) → R-CH(OMTPA)-CO₂Me  R,S-diastereoisomer

R-CH(OH)-CO₂H (4,5,7,9,11,13,15) → R-CH(OMTPA)-CO₂Me  R,R-diastereoisomer

MTPA = −C(=O)−C(OMe)(Ph)(CF₃)

| | | ¹H-NMR chemical shifts (270 MHz, CDCl₃) | | | |
|---|---|---|---|---|---|
| | | CO₂Me* | | CF₃C—O—Me* | |
| 2-hydroxy acid derivatives | | R,S | R,R | R,S | R,R |
| CH₃-CH=CH-CH(OH)-CO₂H | 1,4 | 3.76 | 3.79 | 3.55 | 3.65 |
| CH₂=C(CH₃)-CH(OH)-CO₂H | 2,5 | 3.77 | 3.81 | 3.56 | 3.66 |

TABLE 4-continued $^1$H—NMR chemical shifts (δ) of (R)-Mosher derivatives prepared from compounds 1–15

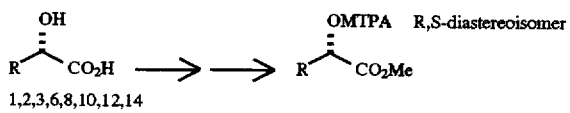

1,2,3,6,8,10,12,14

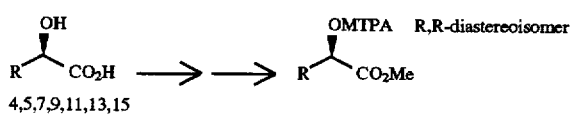

4,5,7,9,11,13,15

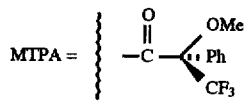

| 2-hydroxy acid derivatives | | $^1$H-NMR chemical shifts (270 MHz, CDCl$_3$) | | | |
|---|---|---|---|---|---|
| | | CO$_2$Me$^a$ | | CF$_3$C—O—Me$^a$ | |
| | | R,S | R,R | R,S | R,R |
| OH / Ph—=—*—CO$_2$H | 3 | 3.78 | 3.82$^b$ | 3.60 | 3.70$^b$ |
| O / OH / —C(=O)CH$_2$—*CH(OH)CO$_2$H | 6, 7 | 3.75 | 3.80 | 3.54 | 3.64 |
| iPr-C(=O)CH$_2$-*CH(OH)CO$_2$H | 8, 9 | 3.75 | 3.79 | 3.52 | 3.64 |
| Ph-C(=O)CH$_2$-*CH(OH)CO$_2$H | 10, 11 | 3.78 | 3.83 | 3.53 | 3.64 |
| C$_5$H$_{11}$-C(=O)CH$_2$-*CH(OH)CO$_2$H | 12, 13 | 3.75 | 3.79 | 3.52 | 3.64 |
| Ph-CH$_2$CH$_2$-*CH(OH)CO$_2$H | 14, 15 | 3.71 | 3.74 | 3.59 | 3.68 |

$^a$Correlation of chemical shifts with absolute configuration at C-2: in all cases the signal for the R,R-diastereoisomer appears downfield relative to that for the R,S-diastereoisomer.
$^b$Measured from NMR spectrum of racemic standard.

We claim:

1. A process for the production of a homochiral 2-hydroxy carboxylic acid or salt thereof corresponding to the following general formula:

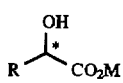

wherein R represents one of the following:

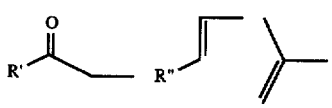

wherein R' represents phenyl optionally para-substituted with methyl, methoxy, nitro or amino; and R" represents hydrogen, halogen or phenyl optionally parasubstituted with methyl, methoxy, nitro or amino; and M represents hydrogen or a salt-forming moiety; characterized in that it comprises reducing a corresponding 2-keto carboxylic acid or salt thereof using a (R)- or (S)-lactate dehydrogenase obtained from *Bacillus stearothermophilus* or *Staphylococcus epidermis*.

2. The process of claim 1 wherein the dehydrogenase is a (S)- lactate dehydrogenase obtained from *Bacillus stearothermophilus*.

3. The process of claim 2 wherein the homochiral 2-hydroxy carboxylic acid is (S)-2-hydroxy-4-oxo-4-phenylbutanoic acid.

4. The process of claim 1 wherein the dehydrogenase is a (R)- lactate dehydrogenase obtained from *Staphylococcus epidermis*.

5. A process as claimed in claim 1 wherein the reduction is effected in combination with a recycling NADH reaction.

6. A process as claimed in claim 1 wherein moiety M represents sodium or potassium and/or the alkyl group R' has up to 6 carbon atoms.

* * * * *